(12) United States Patent
Sekido

(10) Patent No.: US 10,456,013 B2
(45) Date of Patent: Oct. 29, 2019

(54) CABLE CONNECTION STRUCTURE, IMAGING APPARATUS, AND ENDOSCOPE

(71) Applicant: OLYMPUS CORPORATION, Tokyo (JP)

(72) Inventor: Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/161,197

(22) Filed: Oct. 16, 2018

(65) Prior Publication Data

US 2019/0046014 A1    Feb. 14, 2019

Related U.S. Application Data

(63) Continuation of application No. PCT/JP2016/063440, filed on Apr. 28, 2016.

(51) Int. Cl.
*A61B 1/00* (2006.01)
*A61B 1/04* (2006.01)
(Continued)

(52) U.S. Cl.
CPC .......... *A61B 1/00124* (2013.01); *A61B 1/04* (2013.01); *A61B 1/051* (2013.01); *H01R 24/50* (2013.01); *H01R 2103/00* (2013.01)

(58) Field of Classification Search
CPC ....... A61B 1/00124; A61B 1/051; A61B 1/04; H01R 24/50; H01R 2103/00
See application file for complete search history.

(56) References Cited

U.S. PATENT DOCUMENTS 6,635,865 B1 * 10/2003 Soltyk ............... H04N 1/02805
250/208.1
2002/0080233 A1 * 6/2002 Irion ................... H04N 5/2251
348/65

(Continued)

FOREIGN PATENT DOCUMENTS

JP    2008034207 A    2/2008
JP    2009027709 A    2/2009

(Continued)

OTHER PUBLICATIONS

International Search Report dated Aug. 2, 2016 issued in PCT/JP2016/063440.

*Primary Examiner* — Hoa C Nguyen
(74) *Attorney, Agent, or Firm* — Scully, Scott, Murphy & Presser, P.C.

(57) ABSTRACT

A disclosed cable connection structure includes a circuit board that includes a first main body portion and a second main portion that includes a shield set portion, a shield connection electrode, and a plurality of core wire connection electrodes; and a plurality of coaxial cables each of which is processed such that a core wire, an internal insulator, and a shield are exposed from a tip portion in a stepwise manner, where the core wires are connected to the respective core wire connection electrodes and the shields are collectively connected to the shield connection electrode. The second main body portion and the coaxial cables are positioned within a projection plane of a front surface that is perpendicular to a principal surface of the first main body portion.

12 Claims, 10 Drawing Sheets

(51) Int. Cl.
*A61B 1/05* (2006.01)
*H01R 24/50* (2011.01)
*H01R 103/00* (2006.01)

(56) References Cited

U.S. PATENT DOCUMENTS

| | | | | |
|---|---|---|---|---|
| 2011/0306235 | A1* | 12/2011 | Tanaka | H01R 4/027 |
| | | | | 439/578 |
| 2013/0005181 | A1* | 1/2013 | Yamada | H01R 9/0515 |
| | | | | 439/578 |
| 2013/0310043 | A1* | 11/2013 | Bakker | H04W 36/22 |
| | | | | 455/436 |
| 2014/0066711 | A1* | 3/2014 | Farin | A61B 1/0684 |
| | | | | 600/109 |
| 2016/0037029 | A1* | 2/2016 | Igarashi | G02B 23/2476 |
| | | | | 348/65 |
| 2016/0228088 | A1* | 8/2016 | Okuno | A61B 8/4483 |
| 2016/0287060 | A1* | 10/2016 | Usuda | A61B 1/051 |
| 2016/0372848 | A1 | 12/2016 | Yamada | |
| 2017/0035279 | A1 | 2/2017 | Fujii | |

FOREIGN PATENT DOCUMENTS

| | | |
|---|---|---|
| JP | 5631618 B2 | 11/2014 |
| WO | 2015141800 A1 | 9/2015 |
| WO | 2016042804 A1 | 3/2016 |

* cited by examiner

CABLE CONNECTION STRUCTURE, IMAGING APPARATUS, AND ENDOSCOPE

CROSS-REFERENCE TO RELATED APPLICATION(S)

This application is a continuation of International Application No. PCT/JP2016/063440, filed on Apr. 28, 2016, the entire contents of which are incorporated herein by reference.

BACKGROUND

The present disclosure relates to a cable connection structure, an imaging apparatus, and an endoscope in which coaxial cables and a circuit board are connected.

In the past, an endoscope that is inserted into a subject and observes a subject region has been known and widely used in a medical field or the like. The endoscope is configured such that an imaging module, on which an electronic component, such as an image sensor, is mounted, is provided inside a tip portion of a flexible elongated insertion tool. There is a demand to reduce a diameter and a length of the tip portion of the insertion tool in consideration of ease of introduction to a patient.

In relation to the demand as described above, a known cable connection structure is known in which a core wire of a coaxial cable is connected to a connection electrode provided on a second flat portion or a stepped surface in a circuit board that includes, on a principal surface side, a first flat portion having a flat plate shape, the second flat portion being a plate thinner than the first flat portion, and the stepped surface being an inclined surface or a vertical surface provided at a boundary between the first flat portion and the second flat portion (for example, see Japanese Patent Publication No. 5631618 (referred to as JP5631618).

In JP5631618, it is possible to reduce a mounting height of the coaxial cable, that is, it is possible to reduce a diameter, when used in an imaging apparatus, an endoscope, and the like; however, connection of a plurality of coaxial cables is not taken into account. When a plurality of coaxial cables are connected to a circuit board, positions of the coaxial cables with respect to the circuit board are determined while the coaxial cables are held by a tool or the like, but it is difficult to determine the positions of the plurality of thin coaxial cables with accuracy, and connection operation needs skill. Further, if the positioning accuracy is low, connection strength and reliability are reduced.

As a technology for improving the positioning accuracy of cables, a technology has been disclosed, in which, in an imaging module in which a plurality of core wires of a flexible multi-core cable are connected to an image sensor via a circuit board, a recessed portion is provided on a longitudinal side surface of the circuit board that is provided parallel to an image sensor, and the core wires are housed and connected in the recessed portion in order to prevent the core wires from being spread out and reduce a diameter of the imaging module (for example, see Japanese Laid-open Patent Publication 2009-27709).

SUMMARY

According to a first aspect of the present disclosure, a cable connection structure is provided. The cable connection structure includes a circuit board that includes a first main body portion that has a principal surface, and a second main body portion that is arranged such that a first surface facing the principal surface comes into contact with the first main body portion, wherein the second main body is thinner than the first main body portion at least in one direction along the principal surface, and wherein the second main body has, on the side of a second surface opposed to the first surface, a shield set portion formed of a bottom portion and a wall portion that stands from at least one end portion of the bottom portion, a shield connection electrode formed at least on the bottom portion, and a plurality of core wire connection electrodes; and a plurality of coaxial cables, each of which includes a core wire, an internal insulator that covers an outer circumference of the core wire, a shield that covers an outer circumference of the internal insulator, and an external insulator that covers an outer circumference of the shield, the coaxial cables being processed such that the core wires, the internal insulators, and the shields are exposed in a stepwise manner from tip portions thereof, the core wires being connected to corresponding ones of the core wire connection electrodes, the shields being collectively connected to the shield connection electrode, wherein the second main body portion and the coaxial cables are positioned within a projection plane that is obtained when the principal surface is projected in a direction perpendicular to the principal surface.

According to a second aspect of the present disclosure, an imaging apparatus is provided. The imaging apparatus includes an imaging device that includes a light receiving surface that receives incident light; a sensor element that performs photoelectric conversion on light that has passed through the light receiving surface, and generates electrical signal; and a plurality of sensor electrodes that are provided on a back surface opposite to a surface on which the sensor element is provided; a first circuit board that includes first connection electrodes provided on a front surface and a back surface, wherein the first connection electrode on the front surface is electrically and mechanically connected to the sensor electrodes of the imaging device; and a second circuit board that includes a first main body portion that includes a second connection electrode that is connected to the first connection electrode on the back surface of the first circuit board; and a second main body portion that has a shield set portion formed of a bottom portion and a wall portion, the bottom portion being provided on a surface perpendicular to the back surface of the first circuit board, the wall portion standing from at least one end portion of the bottom portion, a shield connection electrode provided at least on the bottom portion, and a plurality of core wire connection electrodes; and a plurality of coaxial cables, each of which includes a core wire, an internal insulator that covers an outer circumference of the core wire, a shield that covers an outer circumference of the internal insulator, and an external insulator that covers an outer circumference of the shield, the coaxial cables being processed such that the core wires, the internal insulators, and the shields are exposed in a stepwise manner from tip portions thereof, the core wires being connected to the respective core wire connection electrodes, the shields being collectively connected to the shield connection electrode, wherein the first main body portion, the second main body portion, and the coaxial cable are positioned within a projection plane of the light receiving surface of the imaging device.

According to a second aspect of the present disclosure, an imaging apparatus is provided. The imaging apparatus includes an imaging device that includes a light receiving surface that receives incident light; a sensor element that performs photoelectric conversion on light that has passed through the light receiving surface, and generates electrical signal; and a plurality of sensor electrodes that are provided on a back surface opposite to a surface on which the sensor element is provided; a first circuit board that includes first connection electrodes provided on a front surface and a back surface, wherein the first connection electrode on the front surface is electrically and mechanically connected to the sensor electrodes of the imaging device; and a second circuit board that includes a first main body portion that includes a second connection electrode that is connected to the first connection electrode on the back surface of the first circuit board; and a second main body portion that has a shield set portion formed of a bottom portion and a wall portion, the bottom portion being provided on a surface perpendicular to the back surface of the first circuit board, the wall portion standing from at least one end portion of the bottom portion, a shield connection electrode provided at least on the bottom portion, and a plurality of core wire connection electrodes; and a plurality of coaxial cables, each of which includes a core wire, an internal insulator that covers an outer circumference of the core wire, a shield that covers an outer circumference of the internal insulator, and an external insulator that covers an outer circumference of the shield, the coaxial cables being processed such that the core wires, the internal insulators, and the shields are exposed in a stepwise manner from tip portions thereof, the core wires being connected to the respective core wire connection electrodes, the shields being collectively connected to the shield connection electrode, wherein the first main body portion, the second main body portion, and the coaxial cable are positioned within a projection plane of the light receiving surface of the imaging device.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following description, as modes for carrying out the present disclosure (hereinafter, referred to as "embodiments"), an endoscope system including an imaging apparatus will be described. In addition, the present disclosure is not limited by the embodiments below. Further, in the description of the drawings, the same components are denoted by the same signs. Furthermore, it is necessary to note that the drawings are schematic, and relationships between thickness and width of each member, proportion of each member, and the like are different from reality. Moreover, portions having different dimensions and proportions are included among the drawings.

First Embodiment

Figure 1:
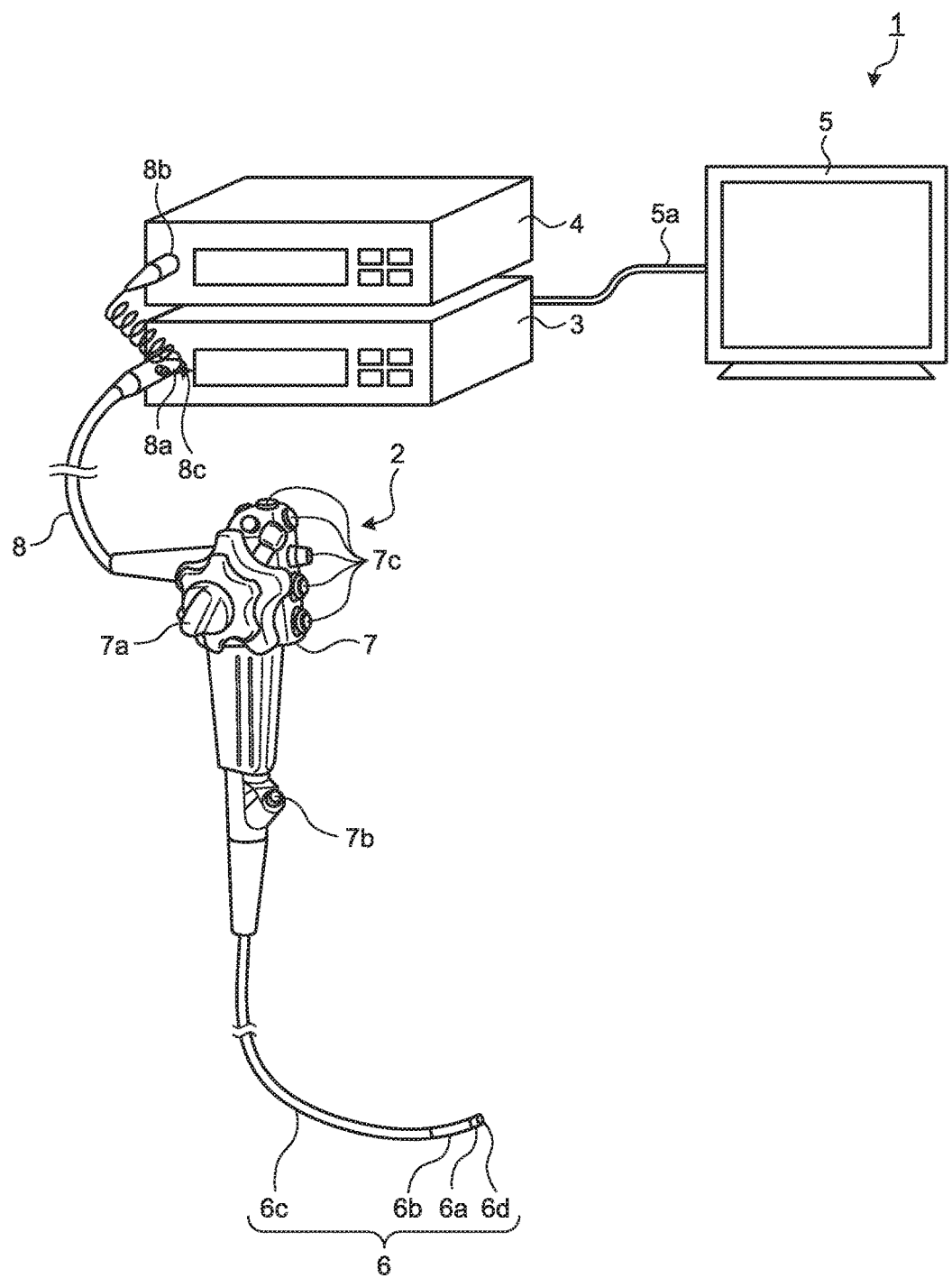
FIG. 1 is a diagram schematically illustrating an overall configuration of an endoscope system according to a first embodiment.

FIG. 1 is a diagram schematically illustrating an overall configuration of an endoscope system according to a first embodiment. As illustrated in FIG. 1, an endoscope system 1 according to the first embodiment includes an endoscope 2 that captures an image inside a subject by being introduced into the subject and generates an image signal inside the subject, an information processing apparatus 3 (external processor) that performs predetermined image processing on the image signal captured by the endoscope 2 and controls each of units of the endoscope system 1, a light source device 4 that generates illumination light for the endoscope 2, and a display device 5 that displays an image of the image signal subjected to the image processing by the information processing apparatus 3.

The endoscope 2 includes an insertion portion 6 that is to be inserted into the subject, an operating unit 7 that is provided on a proximal end portion of the insertion portion 6 and to be held by an operator, and a flexible universal cord 8 that extends from the operating unit 7.

The insertion portion 6 is realized by using an illumination fiber (light guide cable), an electrical cable, an optical fiber, and the like. The insertion portion 6 includes a tip portion 6a inside of which an imaging unit to be described later is provided, a bending portion 6b that is freely bendable and constituted of a plurality of bending pieces, and a flexible tube portion 6c that is provided on a proximal end portion of the bending portion 6b and that has flexibility. In the tip portion 6a, an illumination unit that illuminates the inside of the subject via an illumination lens, an observation unit that captures an image inside the subject, an opening portion in communication with a treatment tool channel, and an air/water supply nozzle (not illustrated) are provided.

The operating unit 7 includes a bending knob 7a for causing the bending portion 6b to bend in the vertical direction and the horizontal direction, a treatment tool insertion portion 7b through which a treatment tool, such as a biopsy forceps or a laser scalpel, is inserted into a body cavity of a subject, and a plurality of switch portions 7c for operating the information processing apparatus 3, the light source device 4, and peripheral devices, such as an air supply device, a water supply device, and a gas supply device. The treatment tool inserted from the treatment tool insertion portion 7b comes out from an opening portion 6d at a distal end of the insertion portion 6 via an internally-provided treatment tool channel.

The universal cord 8 is configured using an illumination fiber, a cable, and the like. The universal cord 8 is bifurcated at a proximal end thereof, and an end portion of one of the branches serves as a connector 8a, and the other end portion serves as a connector 8b. The connector 8a is detachably attached to a connector of the information processing apparatus 3. The connector 8b is detachably attached to the light source device 4. The universal cord 8 propagates illumination light emitted from the light source device 4 to the tip portion 6a via the connector 8b and the illumination fiber. Further, the universal cord 8 transfers an image signal captured by an imaging apparatus to be described later to the information processing apparatus 3 via a cable and the connector 8a.

The information processing apparatus 3 performs predetermined image processing on the image signal output from the connector 8a and controls the entire endoscope system 1.

The light source device 4 is configured using a light source that emits light, a condenser lens, and the like. The light source device 4 emits light from the light source and supplies the light, as illumination light for the inside of the subject as an object, to the endoscope 2 that is connected via the connector 8b and the illumination fiber of the universal cord 8, under the control of the information processing apparatus 3.

The display device 5 is configured of a display using a liquid crystal or organic electro luminescence (EL), or the like. The display device 5 displays various kinds of information including an image subjected to the predetermined image processing by the information processing apparatus 3, via a video cable 5a. With this configuration, an operator is able to observe a desired position inside the subject and determine behaviors thereof by operating the endoscope 2 while viewing an image (in-vivo image) displayed by the display device 5.

Figure 2:
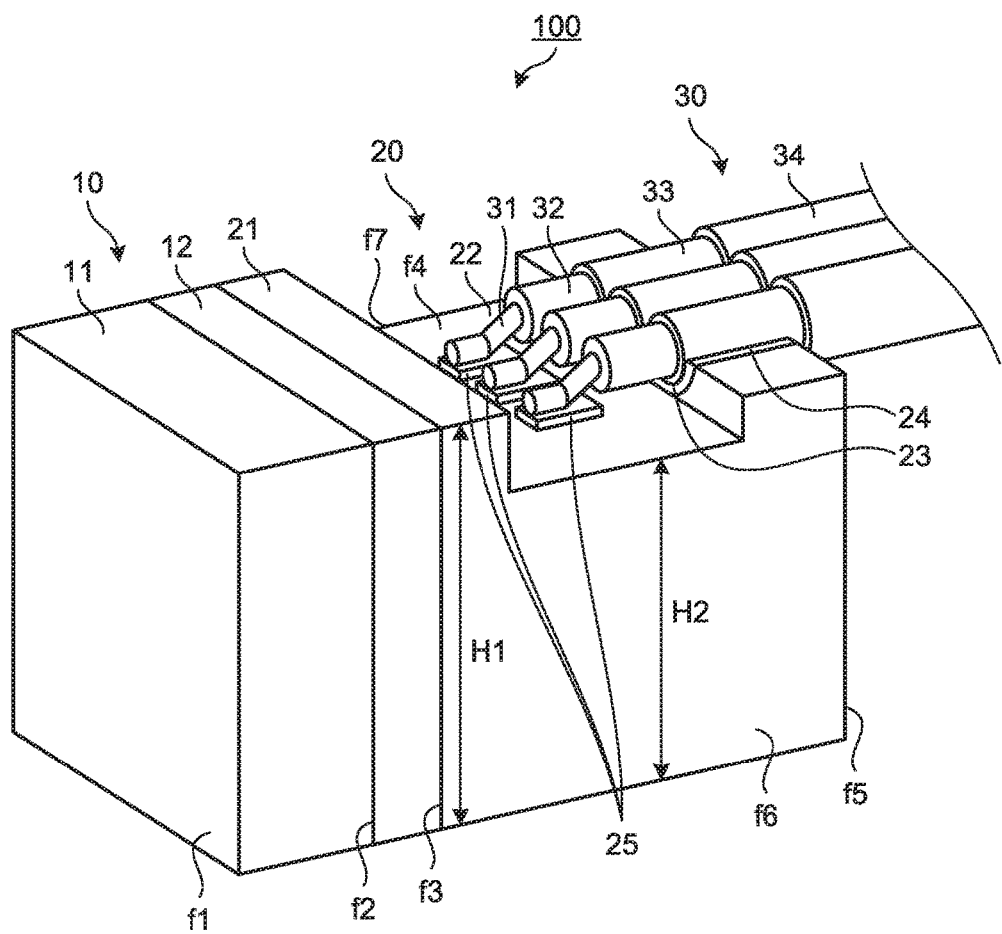
FIG. 2 is a perspective view of an image sensor used in an endoscope illustrated in FIG. 1.
Figure 3:
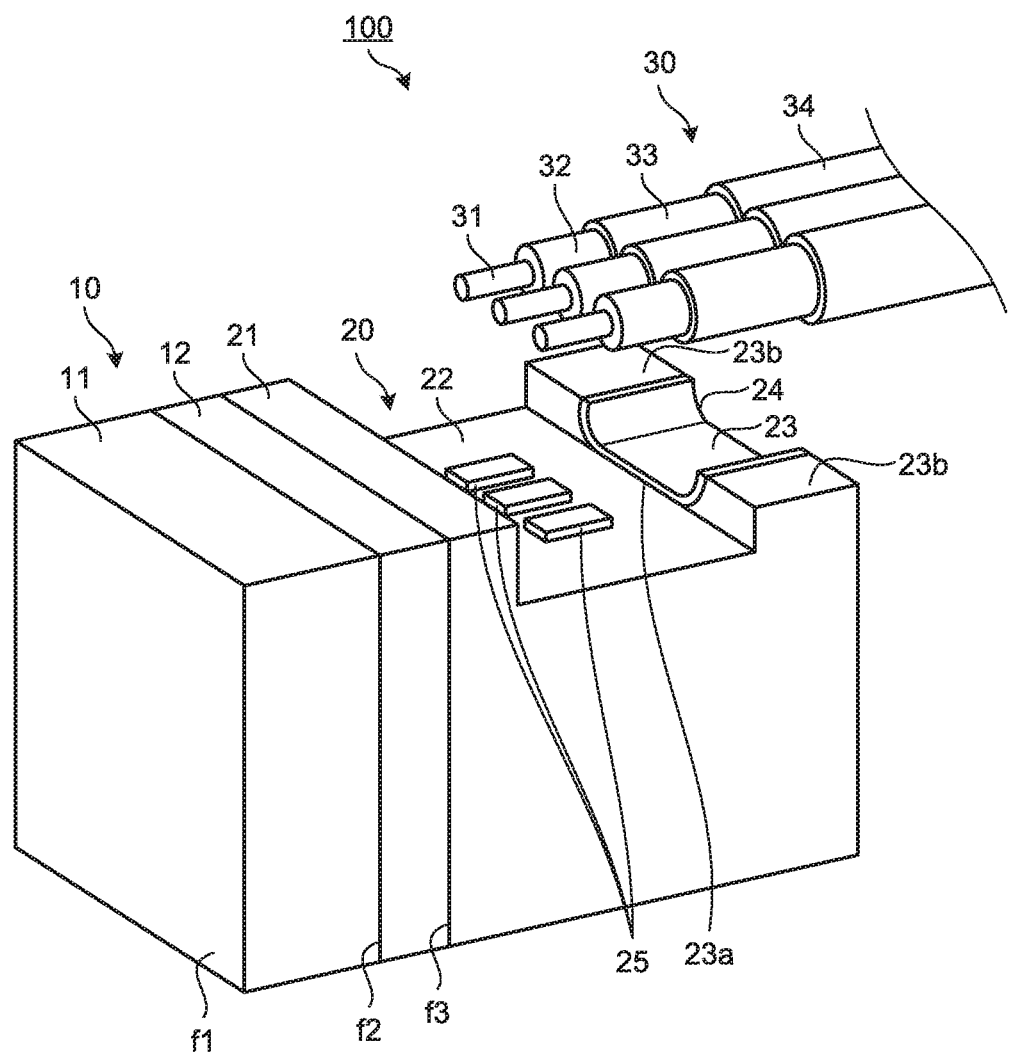
FIG. 3 is a perspective view of a state in which coaxial cables are not connected in the imaging apparatus illustrated in FIG. 2.
Figure 4:
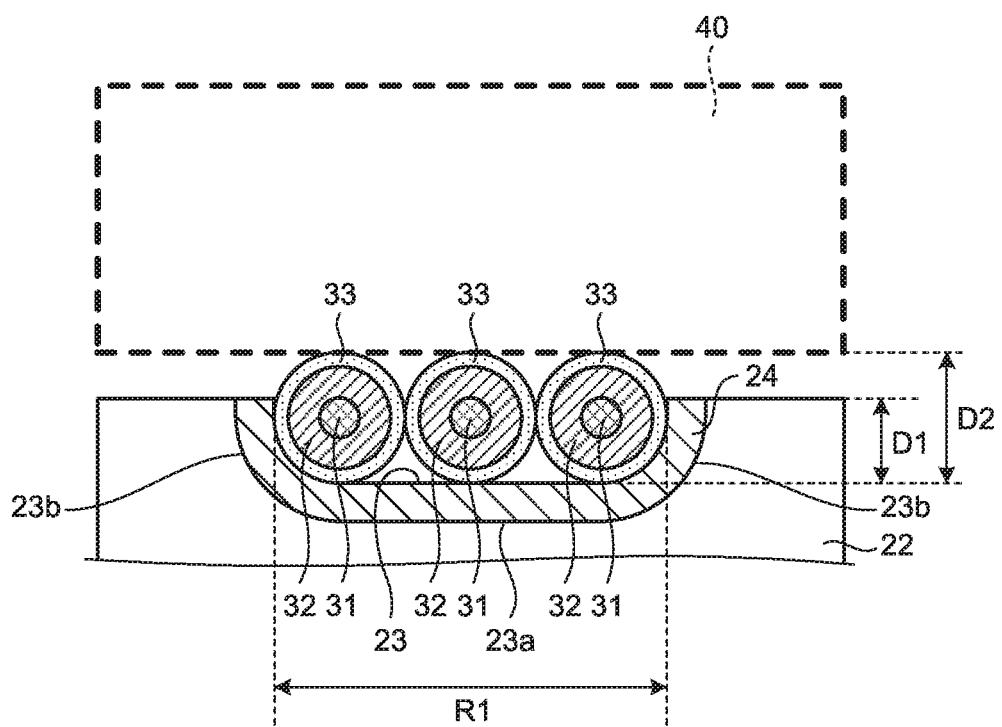
FIG. 4 is a cross-sectional view for explaining connection of shields to a shield connection electrode.

Next, a configuration of the imaging apparatus will be described in detail. FIG. 2 is a perspective view of the imaging apparatus used in the endoscope illustrated in FIG. 1. FIG. 3 is a perspective view illustrating a state in which coaxial cables are not connected in the imaging apparatus illustrated in FIG. 2. FIG. 4 is a cross-sectional view for explaining connection of shields to a shield connection electrode. In FIG. 2 to FIG. 4, illustration of solders used to connect core wires and the shields is omitted.

As illustrated in FIG. 2 and FIG. 3, an imaging apparatus 100 according to the first embodiment includes an image sensor 10, a circuit board 20, and coaxial cables 30.

The image sensor 10 has a structure in which a glass 11 is attached to an image sensor chip 12. Light collected by a lens unit enters a light receiving surface f2 of the image sensor chip 12 that includes a sensor element, via a surface f1 that is a front surface of the glass 11. A sensor electrode (not illustrated) is provided on a back surface of the image sensor 10, where the back surface is opposite to the light receiving surface f2. It is preferable that the image sensor 10 is a chip size package (CSP) formed by performing wiring, electrode formation, resin encapsulation, and dicing on the image sensor chip 12 in a wafer state, and that the size of the image sensor chip 12 finally becomes the size of the package.

The circuit board 20 includes a first main body portion 21 and a second main body portion 22. The first main body portion 21 is provided with a connection electrode (not illustrated) on the side of a surface f3, which is a principal surface that comes into contact with the image sensor 10, and electrically and mechanically connected to the sensor electrode of the image sensor 10. On the side of a top surface f4 of the second main body portion 22, a shield set portion 23 formed of a bottom surface portion 23a and wall portions 23b that stand from both end portions of the bottom surface portion 23a, a shield connection electrode 24 provided on the entire surfaces of the bottom surface portion 23a and the wall portions 23b, and a plurality of core wire connection electrodes 25 are provided. The second main body portion 22 is formed such that a thickness of a side surface portion is thinner than the first main body portion 21, that is, a height H1 of the first main body portion 21 (lengths of side surfaces f6 and f7) is greater than a height H2 of the second main body portion 22 (lengths of the side surfaces f6 and f7).

The shield set portion 23 is provided on the side of a proximal end surface f5 of the second main body portion 22, and the wall portions 23b protrude from the top surface f4 of the second main body portion 22. The shield set portion 23 is a recessed portion formed of the bottom surface portion 23a and the wall portions 23b that stand from the both end portions of the bottom surface portion 23a. The shield connection electrode 24 is provided on the entire surface of the recessed portion; however, as long as the shield connection electrode 24 is provided over the entire width in the width direction of the recessed portion, that is, in a direction perpendicular to a direction (optical axis direction) in which the coaxial cables 30 extend, the shield connection electrode 24 need not be provided over the entire length in the optical axis direction. By providing the shield connection electrode 24 over the entire width of the recessed portion in the width direction, that is, on the bottom surface portion 23a and the wall portions 23b, and connecting the shield connection electrode 24 and shields 33 via bonding materials such as solders (not illustrated), it becomes possible to ensure connection strength and improve reliability. The shield connection electrode 24 may be formed by forming an elongated through hole on a motherboard before singulation of the circuit board 20, subsequently forming a conductive layer in the through hole, and thereafter performing cutting.

The coaxial cable 30 includes a core wire 31 made of a conductive material, an internal insulator 32 that covers an outer circumference of the core wire 31, the shield 33 that covers an outer circumference of the internal insulator 32, and an external insulator 34 that covers an outer circumference of the shield 33. An end portion of the coaxial cable 30 on the side connected to the circuit board 20 is processed such that the core wire 31, the internal insulator 32, and the shield 33 are exposed in a stepwise manner from the tip portion. The exposed core wires 31 are connected to the respective core wire connection electrodes 25, and the exposed shields 33 are collectively connected to the shield connection electrode 24.

As illustrated in FIG. 4, when the shields 33 are connected to the shield connection electrode 24, the three coaxial cables 30 are arranged in the shield set portion 23 while being held by a jig (not illustrated), and thereafter heat and pressure are applied from an upper side by a connection tool 40 to dissolve solders to thereby collectively connect the shields 33 of the three coaxial cables 30 to the shield connection electrode 24. In view of achieving effective heat transfer from the connection tool 40 to the shields 33, it is preferable that the connection tool 40 comes into direct contact with the shields 33, and a height D1 of the wall portions 23b is smaller than a shield diameter D2 of the coaxial cables 30, that is, a diameter of the coaxial cables 30 excluding the external insulators 34 of the coaxial cables 30. By setting the height D1 of the wall portions 23b to be smaller than the shield diameter D2 of the coaxial cables 30, it becomes possible to bring the connection tool 40 into direct contact with the shields 33, so that it becomes possible to improve heat transfer efficiency. If the height D1 of the wall portions 23b is equal to or greater than the shield diameter D2 of the coaxial cables 30, it may be possible to directly heat the shields 33 by the connection tool 40 by setting the size of the connection tool 40 to be smaller than an opening length R1 of the recessed portion. However, it is necessary to prepare the connection tool 40 whose size is adjusted, and it is difficult to align a position of the connection tool 40 with respect to the shields 33; therefore, it is preferable to set the height D1 of the wall portions 23b to be smaller than the shield diameter D2 of the coaxial cables 30.

Furthermore, from the viewpoint of preventing positional deviation of the coaxial cables 30 from the shield set portion 23 and ensuring large connection areas between the shields 33 of the coaxial cables 30 and the wall portions 23b to maintain connection reliability, it is preferable to set the height D1 of the wall portions 23b to be equal to or greater than a half of the shield diameter D2 of the coaxial cables 30.

To easily and accurately align the positions of the three coaxial cables 30 with respect to the shield connection electrode 24, it is preferable to set the opening length R1 of the shield set portion 23 to be equal to or greater than a total length of the shield diameters D2 of the coaxial cables 30 (D2×3) and equal to or smaller than 130% of the total length of the shield diameters D2 of the coaxial cables 30 (D2×3), or preferably, equal to or smaller than 120%, or more preferably, equal to or smaller than 110%. If the opening length R1 of the shield set portion 23 is increased, it becomes possible to cope with variation in the shield diameter and variation in the positions of the coaxial cables; however, to easily and accurately align the positions of the three coaxial cables 30 with respect to the shield connection electrode 24, it is preferable to reduce the opening length R1 of the shield set portion 23.

Figure 5:
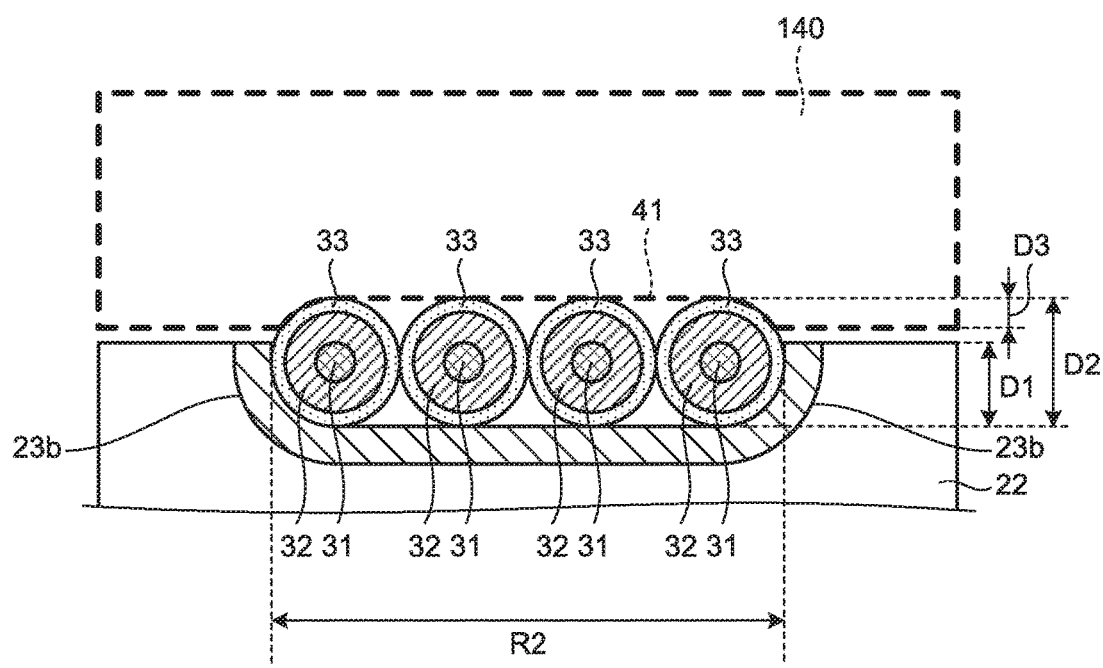
FIG. 5 is a cross-sectional view for explaining connection of the shields to the shield connection electrode.

By using a connection tool 140 as illustrated in FIG. 5, it is possible to more accurately align the positions of the coaxial cables 30. It is preferable to shape the connection tool 140 so as to include a recessed portion 41 such that the coaxial cables 30 are housed in the recessed portion 41. It is preferable to set an opening length R2 of the recessed portion 41 to be equal to the opening length R1 of the shield set portion 23. Further, it is preferable to set a height D3 of the recessed portion 41 to be smaller than a difference between the shield diameter D2 of the coaxial cables 30 and the height D1 of the wall portions 23b.

When the coaxial cables 30 are connected to the circuit board 20, that is, when the shields 33 are connected to the shield connection electrode 24 and the core wires 31 are connected to the core wire connection electrodes 25, the second main body portion 22 and the coaxial cables 30 are positioned within a front surface of the first main body portion 21, where the front surface is perpendicular to the top surface f4, that is, within a projection plane of the surface f3 that is in contact with the image sensor 10. In other words, the second main body portion 22 and the coaxial cable 30 have certain sizes that fall in the projection plane of the first main body portion 21 in the optical axis direction of the image sensor 10. Further, the surface f3 that is the front surface of the first main body portion 21 is formed so as to be substantially identical to the light receiving surface f2 of the image sensor 10. Therefore, the first main body portion 21, the second main body portion 22, and the coaxial cable 30 have certain sizes that fall in the projection plane in the optical axis direction of the image sensor 10. With this configuration, it is possible to reduce a diameter of the imaging apparatus 100.

In the first embodiment, the shield connection electrode 24 is provided on the shield set portion 23 that is a recessed portion; therefore, it is possible to easily align the positions of the plurality of coaxial cables 30 with respect to the shield connection electrode 24, so that it is possible to easily connect the coaxial cables 30 to the circuit board 20. Further, the first main body portion 21, the second main body portion 22, and the coaxial cable 30 are formed in certain sizes that fall in the projection plane in the optical axis direction of the image sensor 10, so that it is possible to reduce the diameter of the imaging apparatus 100.

In the first embodiment as described above, the imaging apparatus 100 using the three coaxial cables 30 has been explained; however, the number of the coaxial cables 30 is not limited to this example. Further, in the first embodiment, the shield set portion 23 is formed of the bottom surface portion 23a and the wall portions 23b that stand from the both end portions of the bottom surface portion 23a; however, the shield set portion 23 may be formed of the bottom surface portion 23a and the wall portion 23b that stands from one end portion of the bottom surface portion 23a. By providing the wall portion 23b on at least one end portion of the bottom surface portion 23a, it becomes possible to regulate the positions of the coaxial cables 30 by the wall portion 23b, so that it becomes possible to easily align the positions of the coaxial cables 30.

Figure 6:
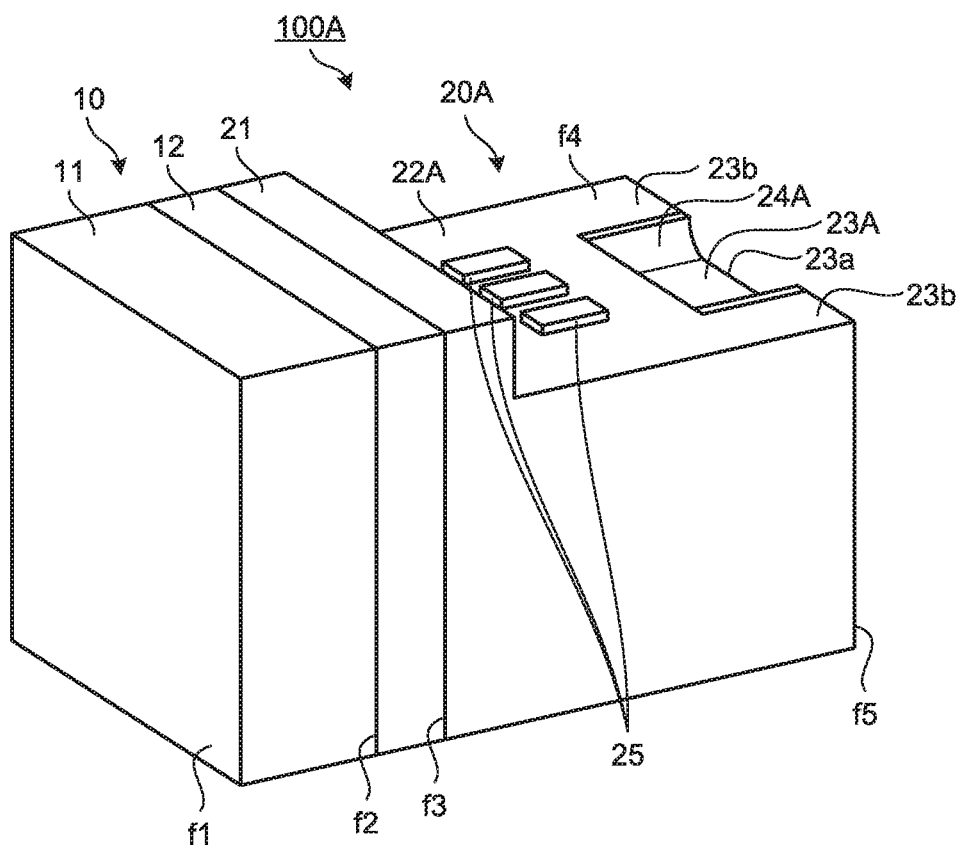
FIG. 6 is a perspective view of an imaging apparatus according to a first modification of the first embodiment of the present disclosure.

Furthermore, in the first embodiment, the shield set portion 23 is formed such that the wall portions 23b protrude from the top surface f4 of the second main body portion 22, but a top surface of the wall portion 23b may be formed so as to be flush with the top surface f4 of the second main body portion 22. FIG. 6 is a perspective view of an imaging apparatus 100A according to a first modification of the first embodiment of the present disclosure. In FIG. 6, the coaxial cables 30 are not illustrated for understanding of the disclosure.

In the imaging apparatus 100A, a circuit board 20A includes the first main body portion 21 and a second main body portion 22A. A shield set portion 23A is provided on the side of the proximal end surface f5 of the second main body portion 22A, and the top surface of the wall portion 23b is flush with the top surface f4 of the second main body portion 22A. The shield set portion 23A is a recessed portion that is formed of the bottom surface portion 23a and the wall portions 23b that stand from the both end portions of the bottom surface portion 23a.

In the imaging apparatus 100A according to the first modification of the first embodiment, the shield set portion 23A is formed such that the top surface of the wall portion 23b is flush with the top surface f4 of the second main body portion 22A; therefore, it is possible to connect the core wires 31 of the coaxial cables 30 to the core wire connection electrodes 25 without bending the core wires 31. With this configuration, it is possible to reduce a mechanical load on the core wires 31 of the coaxial cables 30 and further improve the reliability. Further, similarly to the first embodiment, it is possible to easily align the positions of the plurality of coaxial cables 30 with respect to a shield connection electrode 24A, so that it is possible to easily connect the coaxial cables 30 to the circuit board 20A. Furthermore, the first main body portion 21, the second main body portion 22A, and the coaxial cables 30 are formed in certain sizes that fall in a projection plane of the light receiving surface f2 of the image sensor 10; therefore, it is possible to reduce a diameter of the imaging apparatus 100A.

Figure 7:
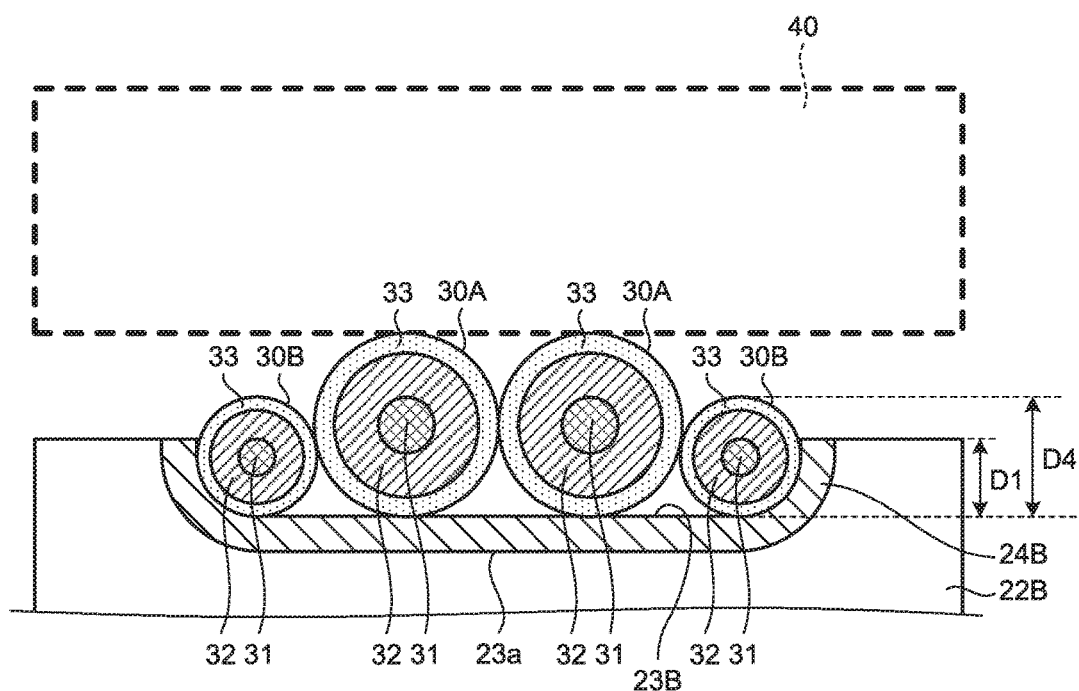
FIG. 7 is a cross-sectional view of an imaging apparatus according to a second modification of the first embodiment of the present disclosure.

Moreover, in the first embodiment, the imaging apparatus 100 using the coaxial cables 30 having the same outer diameters has been explained; however, it may be possible to use coaxial cables having different outer diameters, and collectively connect shields of the coaxial cables to a shield connection electrode. FIG. 7 is a cross-sectional view of an imaging apparatus according to a second modification of the first embodiment of the present disclosure.

In the second modification of the first embodiment, two coaxial cables 30A and two coaxial cables 30B of different kinds, that is, a total of four cables, are used. The outer diameters of the coaxial cables 30A are greater than the outer diameters of the coaxial cables 30B. The coaxial cables 30A are arranged on the inner side of a shield set portion 23B, and the coaxial cables 30B are arranged on the outer side.

When the coaxial cables 30A and 30B having different outer diameters are arranged in the shield set portion 23B, it is preferable to set the height D1 of the wall portions 23b to be equal to or greater than a half of a shield diameter D4 of the coaxial cables 30B that are arranged adjacent to the wall portions 23b, and smaller than the shield diameter D4. Further, it is preferable to set the height D1 of the wall portions 23b to be equal to or greater than a half of the shield diameter D4 of the coaxial cables 30B that are adjacent to the wall portions 23b, from the view point of preventing the coaxial cables 30A and 30B positionally deviating from the shield set portion 23B and ensuring large connection areas between the shields 33 of the coaxial cables 30 and the wall portions 23b to maintain connection reliability.

Although not illustrated, when the coaxial cables 30A having a greater diameter are arranged on the outer side of the shield set portion 23B and the coaxial cables 30B are arranged on the inner side, it is sufficient to set the height D1 of the wall portions 23b to be equal to or greater than a half of the shield diameter of the coaxial cables 30A that are arranged adjacent to the wall portions 23b, and smaller than the shield diameter. Further, it is preferable to set the height D1 of the wall portions 23b to be equal to or greater than a half of the shield diameter of the coaxial cables 30A that are adjacent to the wall portions 23b.

In the second modification, a case has been explained in which the coaxial cables 30A and 30B having different outer diameters are used; however, the same applies to a case in which a plurality of coaxial cables (with the same outer diameter) and one or more single-wire cables are used, for example. When a single-wire cable is connected to a shield connection electrode together with the shields 33 of the coaxial cables, it is sufficient to connect the single-wire cable is connected to the shield connection electrode via an external insulator (without removing the external insulator).

Figure 8:
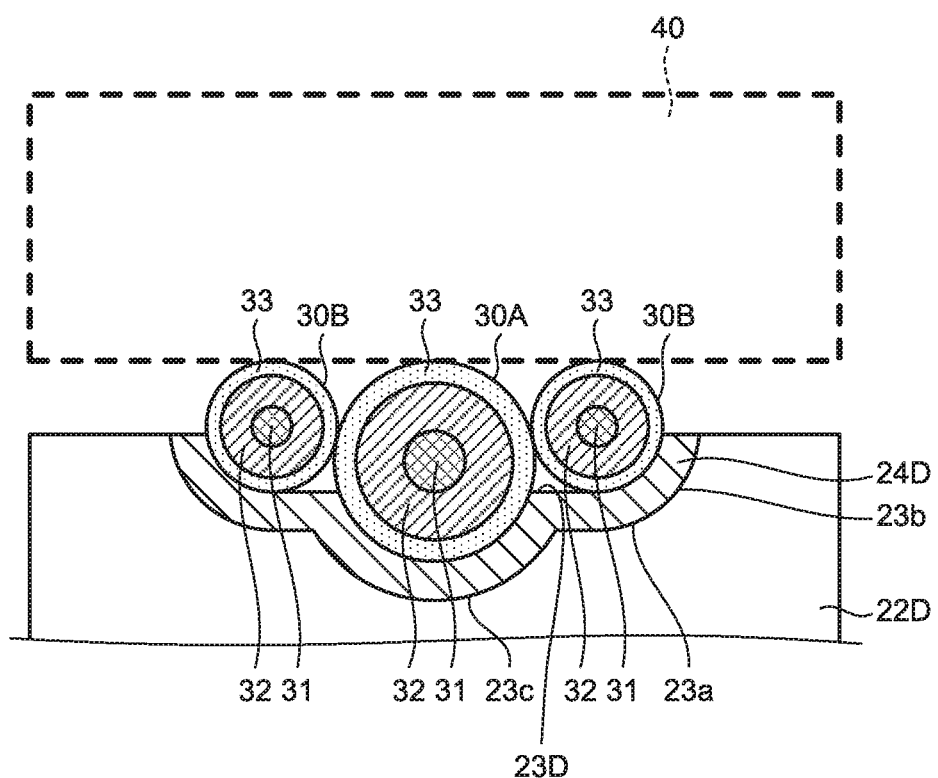
FIG. 8 is a cross-sectional view of an imaging apparatus according to a third modification of the first embodiment of the present disclosure.

Furthermore, when the coaxial cables 30A and 30B having different outer diameters are used, it may be possible to provide a groove on a bottom surface of the shield set portion. FIG. 8 is a cross-sectional view of an imaging apparatus according to a third modification of the first embodiment of the present disclosure.

In the third modification of the first embodiment, one coaxial cable 30A with a large outer diameter and two coaxial cables 30B with small outer diameters are used. The coaxial cable 30A is arranged on the inner side of a shield set portion 23D, and the coaxial cables 30B are arranged on the outer side.

In the shield set portion 23D, a groove 23c is provided at an arrangement position of the coaxial cable 30A in the bottom surface portion 23a. A shield connection electrode 24D is provided on the entire surface of the bottom surface portion 23a including the groove 23c and the wall portions 23b. The groove 23c has a circular arc shape, and therefore, the shield connection electrode 24 that is provided approximately uniformly on the groove 23c comes into contact with the shield 33 of the coaxial cable 30A. It is sufficient to set a depth of the groove 23c such that when the coaxial cables 30A and 30B are arranged in the shield set portion 23D, topmost portions of the coaxial cables 30A and 30B are at the same height.

By providing the groove 23c in the bottom surface portion 23a such that the topmost portions of the coaxial cables 30A and 30B are at the same height, it is possible to bring all of the coaxial cables into contact with the connection tool 40 having a flat bottom surface. Therefore, when heat and pressure are applied from an upper side by the connection tool 40, it is possible to uniformly add the pressure to the coaxial cables 30A and 30B, so that it is possible to prevent deformation of the coaxial cable 30A and improve the reliability.

Figure 9:
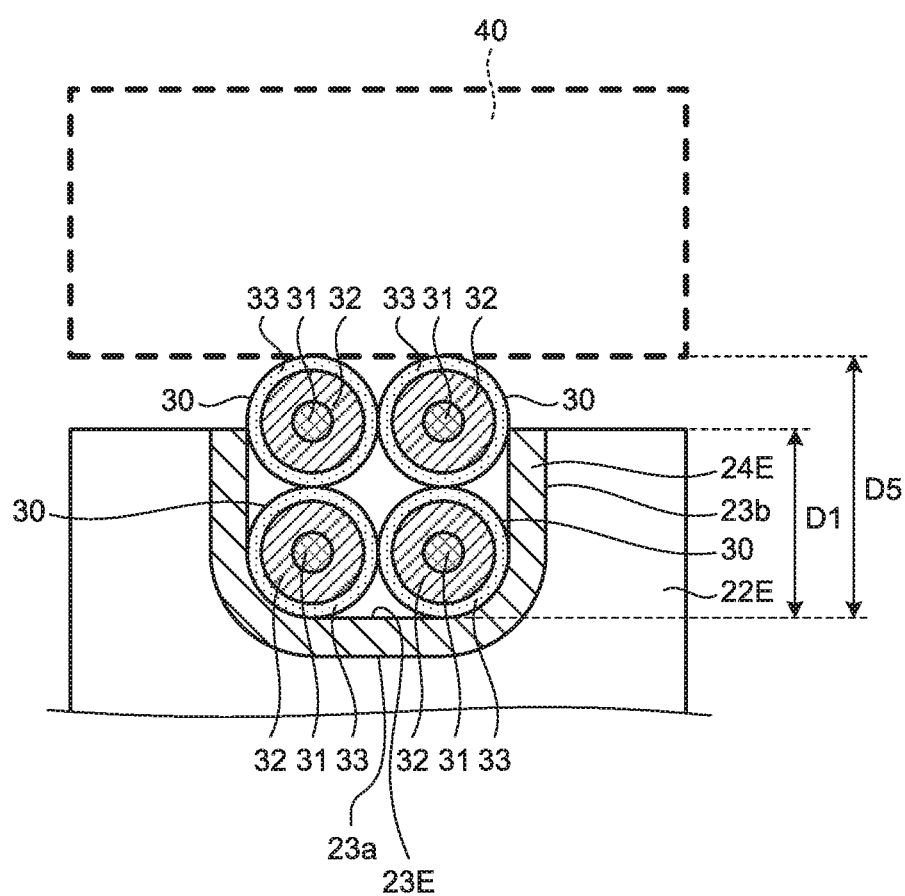
FIG. 9 is a cross-sectional view of an imaging apparatus according to a fourth modification of the first embodiment of the present disclosure.

Further, it may be possible to arrange coaxial cables in the shield set portion in a multi-layer manner. FIG. 9 is a cross-sectional view of an imaging apparatus according to a fourth modification of the first embodiment of the present disclosure.

In the fourth modification of the first embodiment, the four coaxial cables 30 are arranged in a shield set portion 23E in a two-layer manner, where two cables are provided in each layer. It is preferable to set the height D1 of the wall portions 23b of the shield set portion 23E to be smaller than a height D5, which corresponds to twice the diameter of the two coaxial cables 30.

By arranging the coaxial cables 30 in the shield set portion 23E in a multi-layer manner, it is possible to reduce a width size of a circuit board 20E.

Second Embodiment

Figure 10:
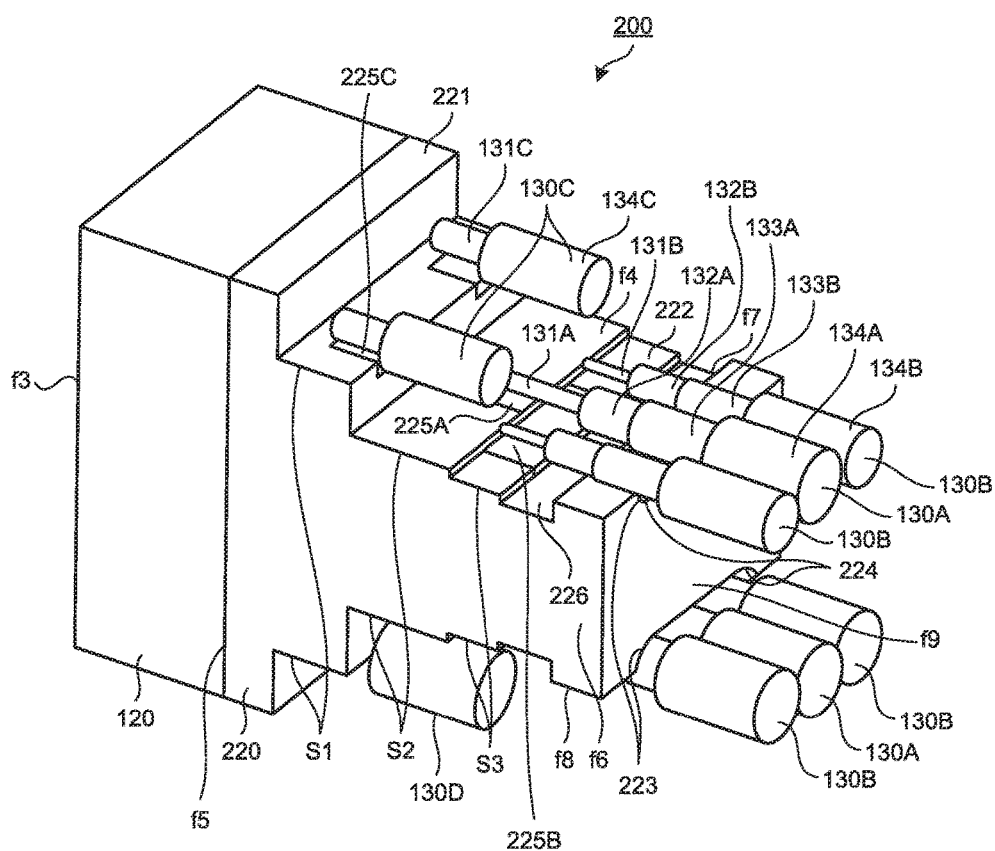
FIG. 10 is a perspective view illustrating a circuit board used in an imaging apparatus according to a second embodiment of the present disclosure.

In an imaging apparatus according to a second embodiment, a circuit board includes a first circuit board and a second circuit board. FIG. 10 is a perspective view illustrating a circuit board 200 used in the imaging apparatus according to the second embodiment of the present disclosure. In FIG. 10, arrangement positions of cables to be used are simply illustrated for understanding of the disclosure.

The circuit board 200 includes a first circuit board 120 that includes an electronic component mounted on the board or mounted inside the board (not illustrated), and a second circuit board 220 that connects coaxial cables 130A and 130B and single-wire cables 130C and 130D.

The second circuit board 220 includes a first main body portion 221 that is electrically and mechanically connected to the first circuit board 120, and a second main body portion 222 that is connected to the coaxial cables 130A and 130B and the single-wire cables 130C and 130D.

In the second main body portion 222, step portions S1, S2, and S3 are provided on a surface f4 and a surface f8. The step portions S1 to S3 are formed so as to approach each other on a proximal end side in the optical axis direction of the imaging apparatus.

The step portion S1 is provided with core wire connection electrodes 225C and 225D (not illustrated) for connecting core wires 131C and 131D (not illustrated) of the single-wire cables 130C and 130D, respectively. The step portion S2 is provided with a core wire connection electrode 225A for connecting a core wire 131A of the coaxial cable 130A. The step portion S3 is provided with a core wire connection electrode 225B for connecting core wires 131B of the coaxial cables 130B, and a shield connection electrode 224 for connecting shields 133A and 133B of the coaxial cables 130A and 130B. The shield connection electrode 224 is disposed on the side of a proximal end surface f9 of the second main body portion 222. The shield connection electrode 224 is provided on the entire surface or a part of the surface of a shield set portion 223 that has a recessed shape. The shields 133A and 133B of the coaxial cables 130A and 130B are arranged in the shield set portion 223 having the recessed shape and connected to the shield connection electrode 224; therefore, it is possible to easily and accurately perform connection.

A groove 226 is provided between the core wire connection electrode 225B and the shield set portion 223 on the step portion S3 in a direction perpendicular to a cable extending direction, in order to prevent occurrence of short circuit.

The second main body portion 222, the single-wire cables 130C and 130D, and the coaxial cables 130A and 130B have certain sizes that fall in a front surface of the first main body portion 221, where the front surface is perpendicular to the top surface f4, that is, a projection plane of a surface f5 that is in contact with the first circuit board 120. Further, the first circuit board 120 is formed so as to be flush with the image sensor 10; therefore, the first main body portion 221, the second main body portion 222, the single-wire cables 130C and 130D, and the coaxial cables 130A and 130B have certain sizes that fall in the projection plane of the image sensor 10. With this configuration, it is possible to reduce a diameter of the imaging apparatus.

A cable connection structure, an imaging apparatus, and an endoscope according to the present disclosure are able to reduce a thickness of a connection portion between cables and a circuit board, that is, reduce an outer size, easily align positions of coaxial cables, and improve connection reliability.

What is claimed is:

1. A cable connection structure comprising:
    a circuit board that includes
        a first main body portion that has a principal surface, and
        a second main body portion that is arranged such that a first surface facing the principal surface comes into contact with the first main body portion, wherein the second main body is thinner than the first main body portion at least in one direction along the principal surface, and wherein the second main body has, on the side of a second surface opposed to the first surface, a shield set portion formed of a bottom portion and a wall portion that stands from at least one end portion of the bottom portion, a shield connection electrode formed at least on the bottom portion, and a plurality of core wire connection electrodes; and
    a plurality of coaxial cables, each of which includes a core wire, an internal insulator that covers an outer circumference of the core wire, a shield that covers an outer circumference of the internal insulator, and an external insulator that covers an outer circumference of the shield, the coaxial cables being processed such that the core wires, the internal insulators, and the shields are exposed in a stepwise manner from tip portions thereof, the core wires being connected to corresponding ones of the core wire connection electrodes, the shields being collectively connected to the shield connection electrode, wherein
    the second main body portion and the coaxial cables are positioned within a projection plane that is obtained when the principal surface is projected in a direction perpendicular to the principal surface.

2. The cable connection structure according to claim 1, wherein
    the shield set portion is a recessed portion that is formed of a bottom portion and wall portions that stand from both end portions of the bottom portion, and
    the shield connection electrode is provided over an entire width of the recessed portion in a width direction perpendicular to a direction in which the coaxial cables extend.

3. The cable connection structure according to claim 2, wherein the plurality of coaxial cables are stacked in multiple layers in the shield set portion.

4. The cable connection structure according to claim 3, wherein the height of the wall portion is set such that a half or more of a height of the coaxial cable on a topmost layer of the multiple layers is housed in a radial direction and at least a part of the coaxial cable on the topmost layer protrudes outside of the recessed portion.

5. The cable connection structure according to claim 1, wherein the shield set portion is formed such that a top surface of the wall portion is flush with a top surface of the second main body portion.

6. The cable connection structure according to claim 1, wherein the wall portion of the shield set portion protrudes from a principal surface of the second main body portion.

7. The cable connection structure according to claim 1, wherein a height of the wall portion is equal to or greater than a half of a shield diameter of the coaxial cables and smaller than the shield diameter.

8. The cable connection structure according to claim 1, wherein
    the plurality of coaxial cables include coaxial cables having different outer diameters, and
    the height of the wall portion is equal to or greater than a half of a shield diameter of the coaxial cable arranged adjacent to the wall portion and smaller than the shield diameter.

9. An imaging apparatus comprising:
    an imaging device that includes
        a light receiving surface that receives incident light;
        a sensor element that performs photoelectric conversion on light that has passed through the light receiving surface, and generates an electrical signal; and
        a plurality of sensor electrodes that are provided on a back surface opposite to a surface on which the sensor element is provided;
    a circuit board that includes
        a first main body portion that has a connection electrode; and
        a second main body portion that has a shield set portion formed of a bottom portion and a wall portion that stands from at least one end portion of the bottom portion, a shield connection electrode formed at least on the bottom portion, and a plurality of core wire connection electrodes; and
    a plurality of coaxial cables, each of which includes a core wire, an internal insulator that covers an outer circumference of the core wire, a shield that covers an outer circumference of the internal insulator, and an external insulator that covers an outer circumference of the shield, the coaxial cables being processed such that the core wires, the internal insulators, and the shields are exposed in a stepwise manner from tip portions thereof, the core wires being connected to corresponding ones of the core wire connection electrodes, the shields being collectively connected to the shield connection electrode, wherein the first main body portion, the second main body portion, and the coaxial cable are positioned within a projection plane of the light receiving surface of the imaging device.

10. An endoscope comprising an insertion portion that includes the imaging apparatus according to claim 9 at a distal end thereof.

11. An imaging apparatus comprising:
an imaging device that includes
a light receiving surface that receives incident light;
a sensor element that performs photoelectric conversion on light that has passed through the light receiving surface, and generates electrical signal; and
a plurality of sensor electrodes that are provided on a back surface opposite to a surface on which the sensor element is provided;
a first circuit board that includes first connection electrodes provided on a front surface and a back surface, wherein the first connection electrode on the front surface is electrically and mechanically connected to the sensor electrodes of the imaging device; and
a second circuit board that includes
a first main body portion that includes a second connection electrode that is connected to the first connection electrode on the back surface of the first circuit board; and
a second main body portion that has a shield set portion formed of a bottom portion and a wall portion, the bottom portion being provided on a surface perpendicular to the back surface of the first circuit board, the wall portion standing from at least one end portion of the bottom portion, a shield connection electrode provided at least on the bottom portion, and a plurality of core wire connection electrodes; and
a plurality of coaxial cables, each of which includes a core wire, an internal insulator that covers an outer circumference of the core wire, a shield that covers an outer circumference of the internal insulator, and an external insulator that covers an outer circumference of the shield, the coaxial cables being processed such that the core wires, the internal insulators, and the shields are exposed in a stepwise manner from tip portions thereof, the core wires being connected to the respective core wire connection electrodes, the shields being collectively connected to the shield connection electrode, wherein
the first main body portion, the second main body portion, and the coaxial cable are positioned within a projection plane of the light receiving surface of the imaging device.

12. An endoscope comprising an insertion portion that includes the imaging apparatus according to claim 11 at a distal end thereof.

\* \* \* \* \*